United States Patent [19]

Vedamuthu

[11] 4,172,899

[45] Oct. 30, 1979

[54] **PREPARATION OF CREAMED COTTAGE CHEESE WITH A *STREPTOCOCCUS DIACETILACTIS* MUTANT**

[75] Inventor: Ebenezer R. Vedamuthu, Bradenton, Fla.

[73] Assignee: Microlife Technics, Inc., Sarasota, Fla.

[21] Appl. No.: 712,692

[22] Filed: Aug. 9, 1976

Related U.S. Application Data

[63] Continuation-in-part of Ser. No. 639,052, Dec. 9, 1975.

[51] Int. Cl.² .................... A23C 19/02; A23C 19/14; C12K 1/02; C12K 3/00
[52] U.S. Cl. ........................................ 426/38; 426/43; 426/61; 435/885
[58] Field of Search ............... 426/34, 36, 38, 41, 426/43, 61; 195/59, 96

[56] References Cited

U.S. PATENT DOCUMENTS

| | | | |
|---|---|---|---|
| Re. 28,276 | 12/1924 | Farr | 195/96 |
| 2,971,847 | 2/1961 | Babel et al. | 426/38 |
| 3,048,490 | 8/1962 | Lundstedt | 426/41 X |
| 3,483,087 | 12/1969 | Christensen | 426/38 X |
| 3,968,256 | 7/1976 | Sing | 426/38 |

*Primary Examiner*—David M. Naff
*Attorney, Agent, or Firm*—Ian C. McLeod

[57] ABSTRACT

A novel mutant strain *Streptococcus diacetilactis* NRRL-B-8177 which is particularly adapted for the preparation of creamed Cottage cheese without fermentation (or prior incubation) of the creaming mixture or dressing is described. This strain produces about one-half of the acid produced by *S. diacetilactis* 18–16 which is regarded as the best bacterium that is commercially available for use in Cottage cheese. Improved flavor and prophylaxis against spoilage bacteria of the dressed Cottage cheese is preferably provided by blending a concentrate of the *Streptococcus diacetilactis* NRRL-B-8177 cells with a creaming mixture at less than about 50° F. (10° C.) and then mixing the cold cream mixture with dry Cottage cheese curd cooled to less than about 50° F. and maintaining the temperature at less than about 50° F.

3 Claims, No Drawings

PREPARATION OF CREAMED COTTAGE CHEESE WITH A STREPTOCOCCUS DIACETILACTIS MUTANT

CROSS REFERENCE TO RELATED APPLICATION

This application is a continuation-in-part of pending application Ser. No. 639,052, filed Dec. 9, 1975.

SUMMARY OF INVENTION

The present invention relates to a novel mutant strain of *Streptococcus diacetilactis* particularly adapted for the preparation of creamed Cottage cheese without a preliminary fermentation of the creaming mixture. In particular, the present invention relates to *Streptococcus diacetilactis* NRRL-B-8177 concentrates for use in a creaming mixture without fermentation as a prophylactic against spoilage bacteria.

PRIOR ART

The prior art in the use of bacteria to prepare Cottage cheese creaming mixtures is represented in part by U.S. Pat. Nos. 2,971,847 to Babel et al and 3,323,921 to Moseley et al. The latter patent describes the use of *Streptococcus diacetilactis* 18-16 for this purpose. In these methods, skim milk is fermented with the selected bacterium at temperatures above normal refrigeration, namely 68° to 71.6° F. (20° to 22° C.) for a period of time and then is mixed with the cream dressing. Multiple steps are thus required in preparing the creaming mixture by these methods.

More recently Canadian Pat. No. 979,275 and U.S. Pat. No. 3,968,256 to Sing describe the use of particular concentrated or lyophilized forms of *Streptococcus diacetilactis*, particularly ATCC No. 15346 (also known as 18-16) added to the creaming mixture at a concentration of from $1.0 \times 10^6$ to $2 \times 10^8$ cells per gram of Cottage cheese without fermenting and then blended with the Cottage cheese. Lundstedt U.S. Pat. No. 3,048,490 describes the use of unconcentrated forms in the same manner. Also in my co-pending application Ser. No. 639,052 I have described an improvement on the Sing method. These "non-prefermenting" methods produce very good creamed Cottage cheese. The problem has been that even at low temperatures between 4.4° C. and 10° C. in the Sing method and in my improved method, the 18-16 slowly produces acid which over a period of time gives the Cottage cheese a sour flavor. Also, and even more important, under commercial conditions, temperatures sometimes increase above 10° C., accelerating acid production, and thus causing the Cottage cheese to have a sour flavor.

OBJECTS

It is therefore an object of the present invention to provide a novel mutant strain of *Streptococcus diacetilactis for Cottage cheese which imparts improved flavor without fermenting or incubating the creaming mixtures prior to addition to the Cottage cheese cured. It is also an object of the present invention to provide a mutant strain which even when temperatures exceed* 10° C. (up to 16° C.), produces very little acid during short periods of warm-up that can occur during commercial marketing. It is also an ojbect of the present invention to disclose a mutant strain of *Streptococcus diacetilactis* which provides prophylaxis against the growth of spoilage bacteria in the creamed Cottage cheese. These and other objects will become increasingly apparent by reference to the following description.

GENERAL DESCRIPTION

The present invention relates to a composition which comprises: bacterial cells of *Streptococcus diacetilactis* NRRL-B-8177 which is a mutant of *Streptococcus diacetilactis* 18-16 mixed with a nutrient medium for the bacterial cells which is acceptable for human consumption and wherein the cells are relatively large mutant cocci which produce significantly lower amounts of acid in comparison to the slightly smaller cells of *Streptococcus diacetilactis* 18-16. Preferably the composition contains at least about $10^6$ cells per ml.

It has been found that the compositions of *Streptococcus diacetilactis* NRRL-B-8177 of the present invention impart a desirable diacetyl flavor to the Cottage cheese when present in high numbers of viable and active cells by synthesizing diacetyl at normal refrigeration temperatures with low lactic acid production. Excessive lactic acid production induces a "sour" defect in Cottage cheese.

The mutant *Streptococcus diacetilactis* NRRL-B-8177 was recently deposited by me with the United States Department of Agriculture, 1815 North University Street, Peoria, Ill. and is now available to the public upon request by the identifying number. By inducing mutations in Wild-Type *S. diacetilactis* 18-16 WT and screening for a slow acid producing (relative to WT) mutant, by chance I was able to get a suitable culture, in which I was able to retain several of the desirable characteristics of parent WT strain. The mutant strain: (1) is slow acid producing and does not cause the "sour" flavor defect in Cottage cheese; (2) allows *Leuconostoc cremoris* to grow readily in association with it; and (3) retains the diacetyl producing property and inhibitory activity of its parent.

Strain NRRL-B-8177 is characterized by the fact that it produced $4.5 \times 10^8$ plaque forming units per ml (PFU/ml) when challenged with a phage for 18-16 WT strain. The 18-16 WT strain produced $6.5 \times 10^8$ PFU/ml. The phage is therefore only 69% efficient against the mutant NRRL-B-8177; however, it does show that the mutant strain is derived from the 18-16 WT. The amount of diacetyl produced by NRRL-B-8177 is relatively low as measured by the Pack et al (J. Dairy Science Vol 47, pages 981-986 (1964) method based upon spectrometric measurement of absorption by a color complex produced by diacetyl and specific chemical reagents. NRRL-B-8177 exhibited 0.25 ppm diacetyl in comparison to 18-16 WT with 0.65 ppm diacetyl after 18 hrs at 21° C. Strain 8177 grows readily in a nutrient medium suitable for *Streptococcus diacetilactis* to cell counts above $1.0 \times 10^9$ and has good freezing stability in the presence of glycerol. It has a relatively low lactose utilizing ability and thus produces relatively little acidity in milk (about half that of 18-16 WT). It was equivalent to 18-16 WT in inhibiting *Alcaligenes viscolactis; Pseudomonas fluorescens; P. Viscosa* and *P. aeruginosa* at 45° F. (7.2° C.).

MUTAGENIC PROCEDURE AND PREPARATION OF COMPOSITIONS

The mutagenic procedure chosen is the simplest known. High temperature incubation was chosen to obtain a low-acid producing mutant. Lactic Streptococcus group to which *S. lactis* subsp. *diacetilactis* belongs consists of members of the genus Streptococcus, which are differentiated among other characteristics by their ability to initiate growth at 10° C. and inability to initiate growth (increase in numbers) at 45° C. Based on this premise, 45° C. incubation was chosen to induce the desired mutation.

A freshly propagated culture of the Wild-Type strain 18-16 was transferred into 100 ml of sterile 11% (W/V) reconstituted nonfat dry milk, which had been tempered at 45° C. for at least 20 minutes. The inoculation rate was 5% (V/V). After holding at 45° C. for 3 days, the culture was plated (by the surface spreading technique) on the previously poured, lactose differential agar of Reddy (M. S. Thesis, Iowa State University, Ames, Iowa (1971) at page 45).

The Reddy agar differentiates between bacteria capable of fast acid production and slow or lack of acid production from the disaccharide lactose (which is the principal carbohydrate in dairy products). The medium contains low levels of proteinaceous substances, yeast extract, lactose, a diffusible buffer in the form of dipotassium hydrogen phosphate, a non-diffusible buffer in the form of calcium carbonate, agar, carboxy methyl cellulose, a pH indicator to reveal acid production by individual colonies in the form of bromocresol purple (acid range—yellow, neutral and alkaline range—violet) and bacterial grade agar. The pH of the agar was 6.8±0.1 and the color of the agar at this pH is violet. Fast acid producing *Streptococcus diacetilactis developing on this agar produce large yellow colored colonies with a surrounding yellow zone (due to change of indicator color). Non-acid producing bacteria form white or colorless or translucent colonies. Slow acid producing bacteria form very small yellow colonies. This agar thus allows the differentiation and selection of fast, slow and non-acid producing cells (colonies) from a given culture. For rapid colony formation, the surface spread plates are incubated in a $CO_2$ atmosphere at 32° C.*

SPECIFIC DESCRIPTION

As the first step, a low acid producing (relative to WT) mutant of *S. diacetilactis* 18-16 was isolated. This was accomplished in the following manner:

(1) A milk culture of the WT strain was removed from the liquid nitrogen stock, and propagated once in sterile eleven percent (11%) reconstituted nonfat dry milk (NFDM) (16 hrs at 22° C.).

(2) This culture was used to inoculate 100 ml of sterile eleven percent (11%) reconstituted NFDM at the rate of one percent (1%). The 100 ml milk culture was incubated at 22° C. for 16 hrs.

(3) A 5.0% inoculum from (2) was transferred to another bottle containing 100 ml of sterile eleven percent (11%) reconstituted NFDM, which had been tempered at 45° C. for at least 20 min. After transfer, the bottle was returned to 45° C., and held in the 45° C. incubator for 72 hrs.

(4) At the end of 3 days at 45° C., the culture was checked for diacetyl-acetoin by King's Test (N. King as described in Dairy Industry 13: 860 (1948)) for a positive reaction as a measure of growth. The culture was then plated by surface spread technique on the lactose differential agar of Reddy described above at dilutions ranging from $1 \times 10^{-2}$ through $1 \times 10^{-7}$. The plates were incubated in a carbon dioxide filled jar (Bio-Quest Gas-Pak) at 32° C. for 4 days.

(5) After 4 days, the plates were examined. Several discrete yellow colonies (indicative of normal acid production) and a few large, colorless, transparent colonies were seen in plates spread with $1 \times 10^{-3}$ dilution. The transparent colonies were marked, and a small portion of one such colony was picked with a needle, and a microscopic smear was made. The microscopic smear showed that the colony was made up of cocci. Relatively large cocci (as compared with WT cells) were present in pairs and very short chains.

(6) The remaining portion of the colony examined under the microscope was transferred into a tube of sterile eleven percent (11%) reconstituted NFDM, incubated at room temperature for 72 hrs, and at the end of incubation examined under the microscope. The cells were typically those of lactic Streptococci in pairs or short chains. The mutant culture failed to coagulate milk even after 72 hrs. The WT strain usually coagulates milk after 48 hrs.

(7) The 72 hr milk culture was tested for diacetylacetoin by King's Test, which gave a positive reaction. The results are shown in Table I.

TABLE I

| Strain | King's Test |
|---|---|
| WT | ++++ |
| NRRL-B-8177 | ++ |

(8) To make sure that the isolated culture was indeed a slow acid producer/low acid producer, a ten percent (10%) inoculum of the isolated culture was transferred to another sterile milk tube and incubated at room temperature along with another tube to which one percent (1%) inoculum of WT culture was added. The results are shown in Table II.

TABLE II

| | Coagulation (Room Temperature) | | | | | |
|---|---|---|---|---|---|---|
| Strain | 24 hrs | 48 hrs | 72 hrs | 96 hrs | 120 hrs | 144 hrs |
| 18-16 (1% inoculum) | Neg | Pos | Pos | Pos | Pos | Pos |
| NRRL-B-8177 (10% inoculum) | Neg | Neg | Neg | Neg | Neg | Neg |

This showed that the isolate is relatively a slow acid producer in spite of the 10-fold greater inoculum used.

(9) A portion of the cultures from (8) were tested for diacetyl-acetoin relative to WT strain. The isolate produced diacetyl-acetoin.

(10) Two loops of the cultures from (8) were inoculated into two separate tubes containing Reddy et al's differential broth (J. Milk Food Technology Volume 34, pages 43–45 (1971)), and incubated at 32° C. for 72 hrs and examined. The results are shown in Table III.

TABLE III

| Strains | Color | Gas | $NH_3$ by Nessler's[1] | Growth |
|---|---|---|---|---|
| 18-16 | violet | +++ | +++ | +++ |
| NRRL-B-8177 | violet | +++ | +++ | +++ |

[1]Nessler's reagent is described in Handbook of Chem. & Physics, Chemical Rubber Co., 42nd Ed (1960) at page 1653.

(11) Cultures from (8) were used to run an arbitrary activity (acid producing activity) test in milk as described by Horral and Elliker in J. Dairy Science Volume 30, page 523 (1947). The temperature of the milk is 37.7° C. and the incubation time is 5½ hours. The results are shown in Table IV.

TABLE IV

| Strain | % acidity after 5½ hrs at 37.7° C. (10% inoculum in Horral and Elliker milk) |
|---|---|
| 18-16 | 0.41% |
| NRRL-B-8177 | 0.23% |

These results indicated that the isolate is a low acid producing mutant of WT 18-16 strain.

The preparation of the concentrates of NRRL-B-8177 can be as described in U.S. Reissue Pat. Nos. 28,276 and 28,488. A conventional S. diacetilactis 18-16 growth nutrient medium is used to grow the cells. Some of the nutrient medium is present with the cells even if they are concentrated to a paste of about $10^{15}$ cells per ml and thus the medium must be acceptable for foods for human consumption. Skim milk or derivatives thereof are used in nutrient medium to aid in the growth of the cells. A level of skim milk of about twenty percent (20%) by weight in the fermentation mixture is not exceeded to facilitate ease in separation of the bacterial cells from the fermentation mixture and preferably less than ten percent (10%) skim milk is used. The acid generated during cell growth is neutralized, preferably continuously, such that the final fermentate has a pH between about 6.0 and 7.0. The cells are preferably concentrated, usually with a centrifuge to remove some or all of the liquid. Other techniques for removal of unwanted components and concentration of the fermentation mixture such as by dialysis are known. The concentrates preferably contain at least about $1 \times 10^9$ cells per ml and preferably between 100 to $300 \times 10^9$ cells per ml by the removal of some of the growth nutrient medium. The concentrates are preferably frozen with a freezing stabilizing agent such as a polyhydric alcohol (glycerol), skim milk or skim milk derivatives for storage and shipment prior to use by the dairy and are available commercially.

COTTAGE CHEESE

In the creamed Cottage cheese, the mutant S. diacetilactis NRRL-B-8177 at less than 50° F. (10° C.), slowly grows and generates a very low concentration of lactic acid; however, the normal shelf temperature must be between 40°-45° F. (4.4°-7.2° C.) for a shelf life of about 28 days or less. Very little acid is generated in this period at these temperatures. Also, even when the temperature goes up to 10° C. to 16° C., as can occur during short periods in commercial marketing, the mutant produces very little acid.

Streptococcus diacetilactis 18-16, has the known ability to inhibit spoilage organisms in the Cottage cheese over a substantial storage period. This general characteristic is discussed in a paper published in the Journal of Milk and Food Technology, Vol. 35, No. 6, pages 349-357 (June 1972) and in a publication entitled "Competitive Growth of Streptococcus Diacetilactis in Mixed Strain Lactic Cultures and Cheese" Band D des XVII, Internationalen Milchwirtschaftskongresses Section D 2, pages 611-618, (1966). Streptococcus diacetilacitis NRRL-B-8177 shares this characteristic with its parent even though it produces less acid.

It is known that acetaldehyde is a by-product of S. diacetilactis fermentative action on lactose-citrate systems in milk. When acetaldehyde is accumulated in relatively large amounts, it causes a flavor defect, called "green", in Cottage cheese and certain other fermentated dairy products. The "green" flavor defect preferably is prevented or eliminated by utilizing concentrates of Leuconostoc cremoris or Leuconostoc dextranicum mixed with S. diacetilactis concentrates as described in my application Ser. No. 639,052. L. cremoris particularly possesses high (in relative terms) alcohol dehydrogenase activity which allows the organism to remove or scavenge excess acetaldehyde generated by S. diacetilactis NRRL-B-8177 in the creaming mixture, thus preventing the "green" flavor defect. S. diacetilactis NRRL-B-8177 does not suppress these flavor bacteria. Also, by using L. cremoris or L. dextranicum with NRRL-B-8177, the Leuconostoc can be used at levels of $10^6$ cells per gm of Cottage cheese and the NRRL-B-8177 at levels of $10^4$ or $10^5$ cells per gm of Cottage cheese to make certain that acidity is maintained at a low level.

The fortification of the creaming mixture with soluble citrates, which are naturally present in milk, along with the bacterial concentrates provides additional diacetyl production. This is a reaction known in the prior art.

SPECIFIC DESCRIPTION

Examples 1, 2 and 3 show the preferred method for the preparation of creamed Cottage cheese using S. diacetilactis NRRL-B-8177.

EXAMPLE 1

A frozen concentrate of S. diacetilactis NRRL-B-8177 prepared from skim milk as described in U.S. Reissue Pat. No. 28,276 was used. The skim milk was present in the fermentation mixture at a level of 1.0% by weight. The fermentation mixture was continuously neutralized with anhydrous ammonia gas. The fermentation mixture was centrifuged to produce a concentrate which contained about 150 to $250 \times 10^9$ cells per ml and was mixed with ten percent (10%) by weight glycerol as a freezing stabilizing agent and frozen to −20° F. (−28.9° C.) prior to use. The concentrate was thawed for use in warm chlorinated water (100° F. (37.8° C.); at least 100 ppm available chlorine) for less than 30 minutes.

A pasteurized creaming mixture of by volume 4 parts skim milk and 6 parts of twenty percent (20%) butterfat cream was cooled to a temperature of 40° F. The concentrate was blended into the creaming mixture at a rate of 170 grams of concentrate per 200 gallons (0.757 cubic meters) of creaming mixture for a period of 30 minutes without allowing the temperature to raise above 50° F. (10° C.). The creaming mixture was immediately applied to drained, washed and cooled Cottage cheese curd and packaged. The packages were stored at 40° F. (4.4° C.) or below. Noticeable flavor (diacetyl) developed between 72 and 96 hours at the storage temperature.

The resulting creamed Cottage cheese had an excellent flavor without a sour acid flavor and consistently had a shelf life of 28 days without evidence of the growth of spoilage organisms which are usually present in small quantities in the packaged product.

EXAMPLE 2

The procedure of Example 1 was repeated except that a concentrate of about $1 \times 10^{10}$ cells per ml of Leuconostoc cremoris was added to the creaming mixture in a ratio of one part per part of *S. diacetilactis* NRRL-B-8177. The result was an excellently flavored creamed Cottage cheese without a sour or a "green" flavor. Noticeable flavor developed when stored at 40° F. (4.4° C.) within 24 hours.

EXAMPLE 3

The procedure of Example 1 was repeated except that a sodium citrate solution was added at the rate of two gallons (7570 cc) per 200 gallons (0.757 cubic meters) of creaming mixture to enhance the flavor. The citrate solution was prepared by dissolving 1 pound, 8 ounces (680 grams) of the salt in 2 gallons (7570 cc) of water. Noticeable flavor developed in the Cottage cheese within 24 hours when it was stored at 40° F. (4.4° C.). The product had an excellent flavor because of the increased action of the bacteria on the added citrate to produce diacetyl.

As can be seen from Examples 1 to 3, the compositions of the present invention including NRRL-B-8177 are superior in producing good Cottage cheese. It will be appreciated that the NRRL-B-8177 could be blended with the cooled curd before adding the creaming mixture; however, this is not preferred. The bacterial compositions can be concentrated or unconcentrated forms with the growth nutrient medium. Also, the cells can be lyophilized, however this is also not preferred because of the damaging effect of lyophilization. It is also possible to use the mutant *Streptococcus diacetilactis* as a prophylactic in other products because of its low acid production and its ability to inhibit spoilage bacteria.

I claim:

1. In the method for the preparation of creamed Cottage cheese by providing *Streptococcus diacetilactis* mixed with the curd and cream the improvement which comprises:

inoculating the Cottage cheese with an amount of *Streptococcus diacetilactis* NRRL-B-8177 which is a mutant of *Streptococcus diacetilactis* 18-16 WT sufficient to impart flavor after a period of time at cold storage temperatures.

2. The method of claim 1 wherein the inoculation is at a temperature of less than about 10° C.

3. The method of claim 1 wherein the inoculation is in an amount of between about $10^4$ and $10^8$ cells per gm of Cottage cheese.

* * * * *